(12) United States Patent
Rezach

(10) Patent No.: US 7,942,901 B2
(45) Date of Patent: May 17, 2011

(54) CONNECTOR APPARATUS

(75) Inventor: Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 602 days.

(21) Appl. No.: 11/409,772

(22) Filed: Apr. 24, 2006

(65) Prior Publication Data

US 2007/0270816 A1   Nov. 22, 2007

(51) Int. Cl.
*A61B 17/70* (2006.01)

(52) U.S. Cl. .................................................. 606/250

(58) Field of Classification Search .............. 606/250, 606/251, 278

See application file for complete search history.

(56) References Cited

U.S. PATENT DOCUMENTS

| | | | |
|---|---|---|---|
| 4,653,481 A | 3/1987 | Howland | |
| 5,030,220 A | 7/1991 | Howland | |
| 5,282,801 A | 2/1994 | Sherman | |
| 5,330,473 A | 7/1994 | Howland | |
| 5,601,554 A | 2/1997 | Howland | |
| 5,620,443 A | 4/1997 | Gertzbein | |
| 5,624,442 A * | 4/1997 | Mellinger et al. | 606/278 |
| 5,630,816 A * | 5/1997 | Kambin | 606/252 |
| 5,688,273 A | 11/1997 | Errico | |
| 5,976,135 A | 11/1999 | Sherman et al. | |
| 6,066,140 A | 5/2000 | Gertzbein | |
| 6,083,224 A | 7/2000 | Gertzbein | |
| 6,136,003 A | 10/2000 | Van Hoeck | |
| 6,254,603 B1 | 7/2001 | Gertzbein | |
| 6,283,967 B1 * | 9/2001 | Troxell et al. | 606/252 |
| 6,471,704 B2 | 10/2002 | Gertzbein | |
| 6,602,254 B2 | 8/2003 | Gertzbein | |
| 2004/0111088 A1 | 6/2004 | Picetti | |
| 2005/0228378 A1 * | 10/2005 | Kalfas et al. | 606/61 |
| 2006/0058789 A1 * | 3/2006 | Kim et al. | 606/61 |

FOREIGN PATENT DOCUMENTS

| | | |
|---|---|---|
| JP | 11 244299 A | 9/1999 |
| WO | WO 95/13754 | 5/1995 |
| WO | WO03037200 | 5/2003 |
| WO | WO2006066685 | 6/2006 |

OTHER PUBLICATIONS

Written Opinion of PCT/US2007/065818.

* cited by examiner

*Primary Examiner* — Eduardo C Robert
*Assistant Examiner* — Elana B Fisher

(57) ABSTRACT

A connector apparatus for linking spinal rods comprises a connector body having a C-shaped engagement portion contiguous a closed engagement portion. The engagement portions each include an opening to receive a rod, each opening including an inner contact surface to engage the rod. Additionally, each engagement portion includes a through-hole to receive a screw, the through-holes being aligned substantially perpendicular to a longitudinal axis of the connector body. The through-hole and screw corresponding to the C-shaped engagement portion are offset from the corresponding rod when the rod is positioned in the corresponding opening. Additionally, the screws are advanced through the through-holes to urge the rods against the inner contact surfaces to engage the connector body to the rods. The connector apparatus creates a low profile, top tightening fixation system, providing a stable, rigid transverse connection between adjacent spinal rods.

21 Claims, 5 Drawing Sheets

CONNECTOR APPARATUS

The present disclosure broadly concerns spinal fixation systems and generally relates to a connector apparatus used to connect spinal rods. The apparatus can be useful for correction of spinal injuries or deformities.

BACKGROUND

Several techniques and systems have been developed for use in correcting and stabilizing spinal curvatures, and for facilitating spinal fusion in the case of spinal disorders or degenerative conditions. In some systems, a pair of bendable rods may be longitudinally disposed adjacent the vertebral column and are fixed to various vertebrae along the length of the spine by way of a number of fixation elements, such as hooks and screws. In certain situations, it is desirable to supplement an existing spinal rod connected to the vertebral column with a new spinal rod, to add strength and stability to the fixation system.

Numerous spinal rod systems have been developed which provide transverse connectors for linking the adjacent spinal rods across the spinal midline to provide a rigid and stable construct. Such systems can present one or more difficulties for spinal surgeons. Many of the devices are high profile which increases soft tissue trauma and surgical complications. Moreover, it certain situations it is desirable to provide a transverse connection between adjacent spinal rods on the same side of the spinal midline.

Rigid transverse connections between spinal rods are beneficial because they restrict rod migration and increase construct stiffness. In many cases involving multi-level fusion of the spine, these features are essential while solid bone fusion is accomplished. In the post-operative period before fusion occurs, a significant amount of motion can occur between rods or other elongated members and other structure such as wires and hooks. That motion can, for example, allow a scoliotic correction to decrease or the pelvis to de-rotate towards a previous, deformed position. By providing a rigid transverse connection between two spinal rods, the loss of correction can be reduced and a stiffer construct can be created which may enhance the promotion of a solid fusion. A need remains for low profile devices which link adjacent spinal rods in an easy-loading, top-tightening fashion with a minimum of components and steps, providing increased stability to the fixation system.

DESCRIPTION OF THE ILLUSTRATED EMBODIMENTS

Figure 1:
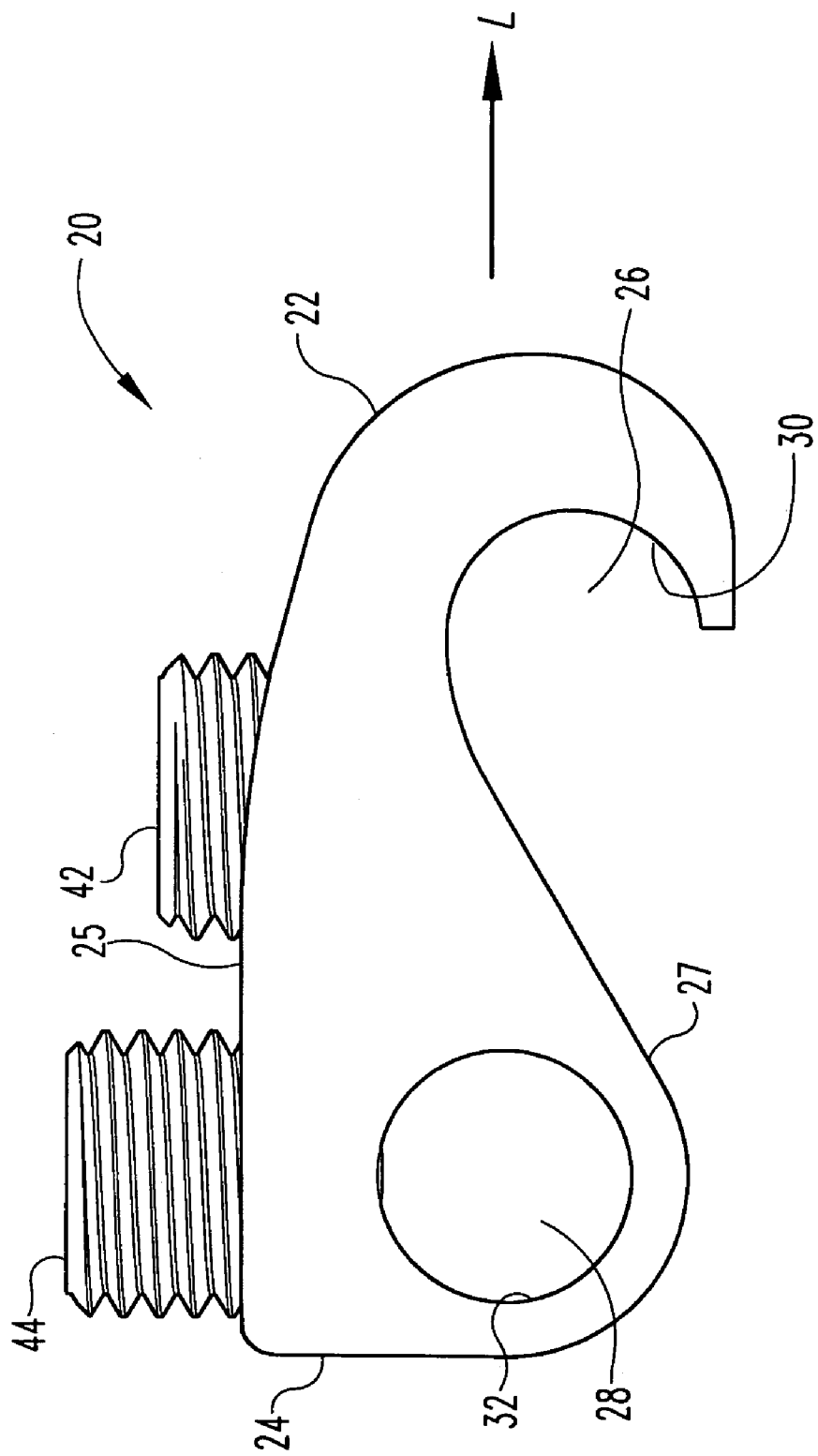
FIG. 1 is a side elevation view of a connector assembly according to an embodiment of the present application.

For the purpose of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

In certain embodiments, a connector apparatus for linking elongate members comprises a connector body having a C-shaped engagement portion contiguous a closed engagement portion. The engagement portions each include an opening to receive an elongate member, each opening having an inner contact surface configured to engage the elongate member. Additionally, each engagement portion includes a through-hole to receive a screw, the through-holes being aligned substantially perpendicular to a longitudinal axis of the connector body. The through-hole and screw corresponding to the C-shaped engagement portion may be offset from the corresponding elongate member when the elongate member is positioned in the corresponding opening. The screws are advanced through the through-holes to contact the elongate members and urge the elongate members against the inner contact surfaces to engage the connector body to the elongate members. The connector apparatus creates a low profile, top loading, top tightening fixation system, providing a stable, rigid system that sufficiently restricts movement and bending of the spinal rods and increases overall rigidity. The connector apparatus also provides a stable, rigid system by combining the strength of a closed engagement portion with the strength, flexibility and convenience of a C-shaped engagement portion.

Referring generally to FIG. 1, there is shown an embodiment of a connector device 20 having a longitudinal axis L. Connector device 20 has a first engagement portion 22 and a second engagement portion 24. First and second engagement portions 22 and 24 may be directly adjacent each other. Additionally, connector device 20 includes a top surface 25 generally parallel with longitudinal axis L. First engagement portion 22 defines a channel 26 and second engagement portion 24 defines an opening 28. In the illustrated embodiment, opening 28 is circular in cross-sectional shape, however it should be appreciated that opening 28 can be shaped differently as would occur to one skilled in the art. Additionally, in the illustrated embodiment, channel 26 is a bottom opening channel. Channel 26 includes an inner contact surface 30 and opening 28 includes an inner contact surface 32. Channel 26 and opening 28 are configured to receive elongate members, such as spinal rods. Tightening members, such as screws 42 and 44, can be used to secure elongate members in channel 26 and opening 28.

Figure 2:
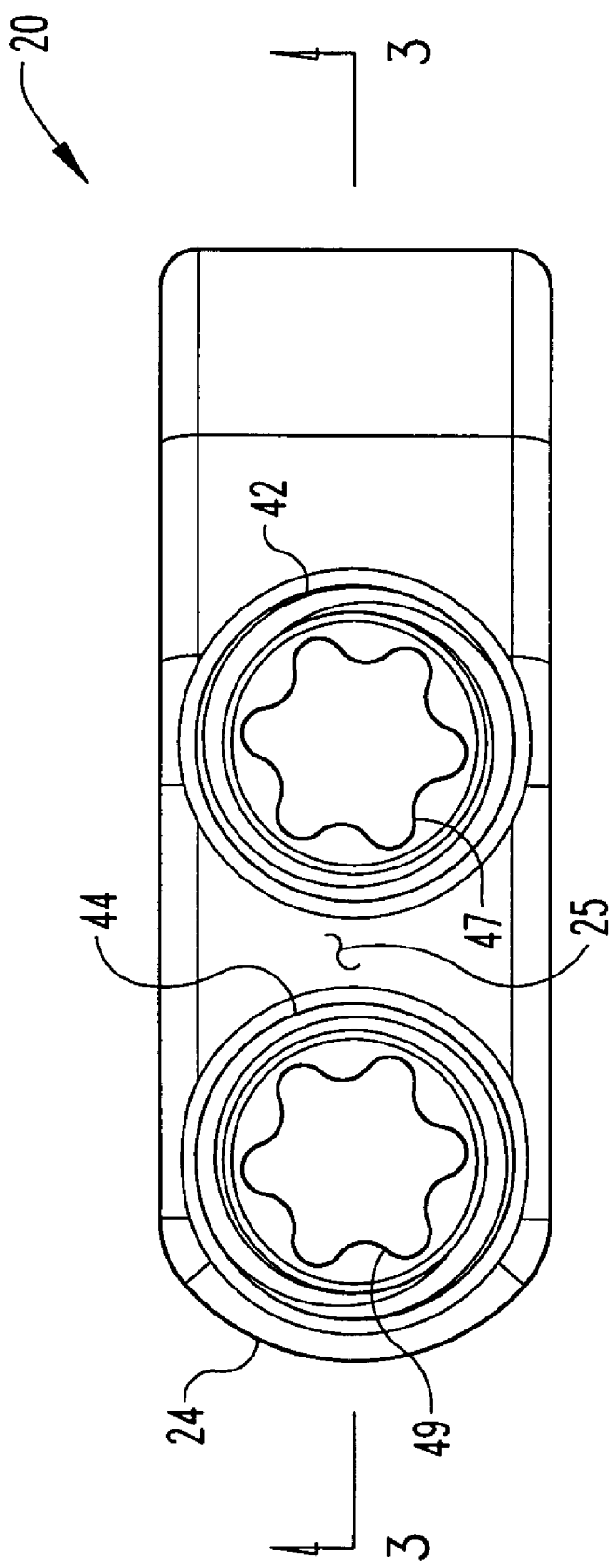
FIG. 2 is a top elevation view of a connector assembly according to an embodiment of the present application.

FIG. 2 illustrates a top view of connector device 20 with screws 42 and 44 positioned in engagement with connector device 20. In certain embodiments, screws 42 and 44 can be inserted to a position where the tops of the screws are below top surface 25. In such embodiments, screws 42 and 44 may rest essentially within connector device 20. In other embodiments, one or both of screws 42 and 44 could include an upper portion, such as a hexagonal head, that remains above top surface 25 of connector device 20. As an example, one or both of screws 42 and 44 could be break-off set screws having break-off top portions. It will be appreciated that screws 42 and 44 could be other appropriate types of screw, or could be replaced by other appropriate locking member(s).

Figure 3:
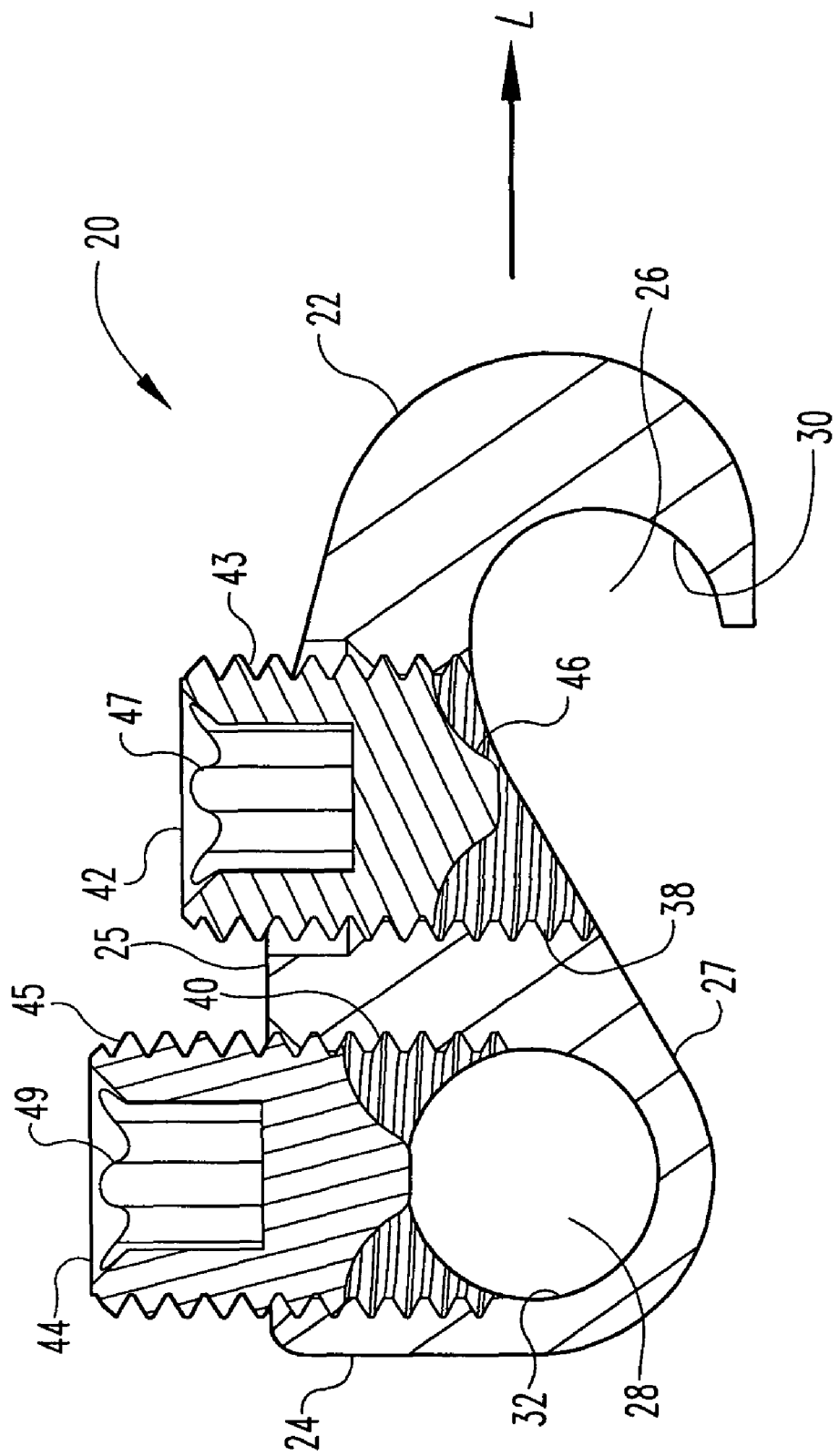
FIG. 3 is a cross-sectional view of the connector assembly of FIG. 2.

FIG. 3 is a cross-sectional view of connector device 20 taken along section lines 3-3 of FIG. 2. As illustrated, first engagement portion 22 defines a through-hole 38 and second engagement portion 24 defines a through-hole 40. Through-holes 38 and 40 are configured to engage with and receive retaining members, such as screws 42 and 44. Through-holes 38 and 40 are aligned substantially perpendicular to top surface 25 of connector device 20. Through-holes 38 and 40 are in communication with channel 26 and opening 28, respectively. Screws 42 and 44 are operable to lock connector device 20 to elongate members such as spinal rods or bars, as further discussed below. Screws 42 and 44 provide a top tightening configuration, with the screws entering through top surface 25 of device 20 and being advanced through through-holes 38 and 40, respectively, to engage connector device 20 to elongate members.

The illustrated embodiment of screws 42 and 44 include threaded portions 43 and 45, respectively, which engage with threaded surfaces of through-holes 38 and 40. Screw 42 includes a bearing surface 46 configured to contact and push a spinal rod into engagement with inner contact surface 30. Bearing surface 46 is shaped to conform to an outer surface of a rod positioned in channel 26. In some embodiments, bearing surface 46 is curved in a similar manner as the curved outer surface of a spinal rod. Additionally, screws 42 and 44 include internal, recessed hexagonal tops 47 and 49 to receive conventional driving tools. In other embodiments, other internal prints or external configurations could be used for accommodating gripping or driving tools.

In preferred embodiments, engagement portion 22 is hook shaped or C-shaped, with through-hole 38 and screw 42 being at least partially offset from the positioning of a spinal rod in channel 26. Engagement portion 22 at least partially surrounds a spinal rod positioned in channel 26. Engagement portion 24 is an all encompassing, closed portion, such that engagement portion 24 and screw 44 completely surround a segment of a spinal rod positioned in opening 28. In the illustrated embodiment, a bottom surface 27 of connector device 20 is generally S-shaped. S-shaped bottom surface 27 gives engagement portion 24 a correspondingly curved bottom surface. Inner contact surface 30 is preferably a segment of bottom surface 27. In other embodiments, engagement portion 24 can be box or squared shaped, or shaped in other closed manners so as to fully surround a segment of a spinal rod.

Figure 4:
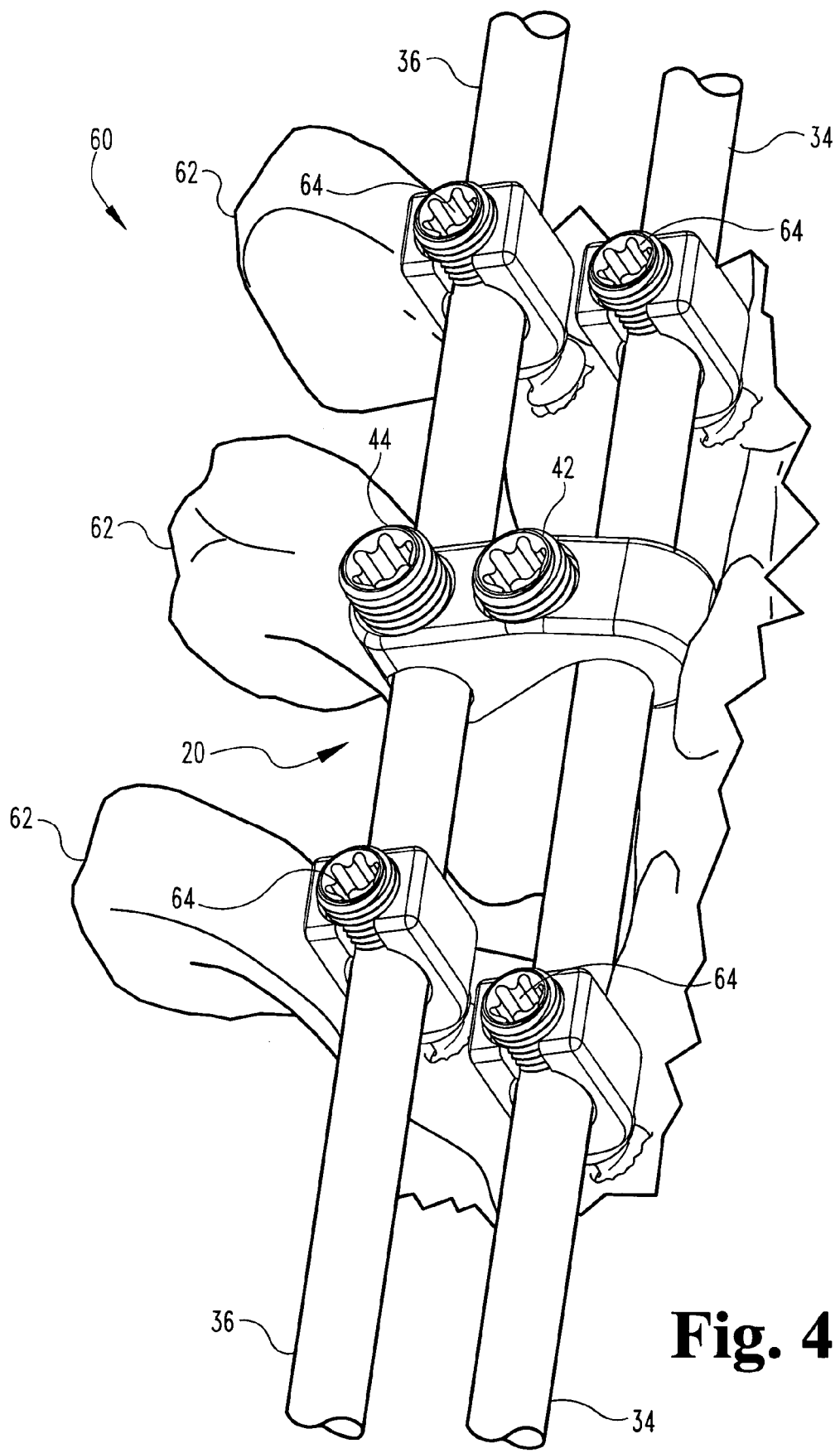
FIG. 4 is a perspective view of a connector assembly relative to vertebrae according to an embodiment of the present application.

Referring generally to FIG. 4, there is shown a perspective view of an embodiment of connector device 20 relative to a section of spine 60 including vertebrae 62. As illustrated, screws 42 and 44 can be advanced through through-holes 38 and 40, respectively, to engage connector device 20 to a first spinal rod 34 and a second spinal rod 36. In the illustrated embodiment, spinal rods 34 and 36 are connected to vertebrae 62 at connection points. Spinal rods 34 and 36 can be connected to vertebrae 62 by pedicle screws 64 that are threaded into respective vertebrae 62, or by other such similar fixation elements.

In certain embodiments, as illustrated, both spinal rods 34 and 36 are positioned on the same side of the spinal midline, or the spinous processes, of vertebrae 62. In other words, spinal rods 34 and 36 can both be positioned between one transverse process and the adjacent spinous process of each relevant vertebra 62. Positioning rods 34 and 36 in this fashion can be done several ways. Rods 34 and 36 can be placed simultaneously, providing a dual-rod construct along a portion of the spine (e.g. FIG. 4), or a construct in which one rod is attached to and extends along one set of vertebrae and is connected to another rod attached to another set of vertebrae (e.g. FIG. 5). Rods 34 and 36 may also be placed separately. For example, if rod 34 has been placed in a previous surgery, another rod 36 can be placed later in a revision surgery. Thus, in the latter situation, existing or previously-placed rod 34 can remain in place, without the necessity to remove tissue that has grown in contact with it or associated implants. Further, positioning rods 34 and 36 somewhat laterally, as shown, avoids the necessity to remove bone material of the spinous processes. In other embodiments, one spinal rod could be positioned on each side of the spinous processes and connector device 20 can cross the spinal midline.

Figure 5:
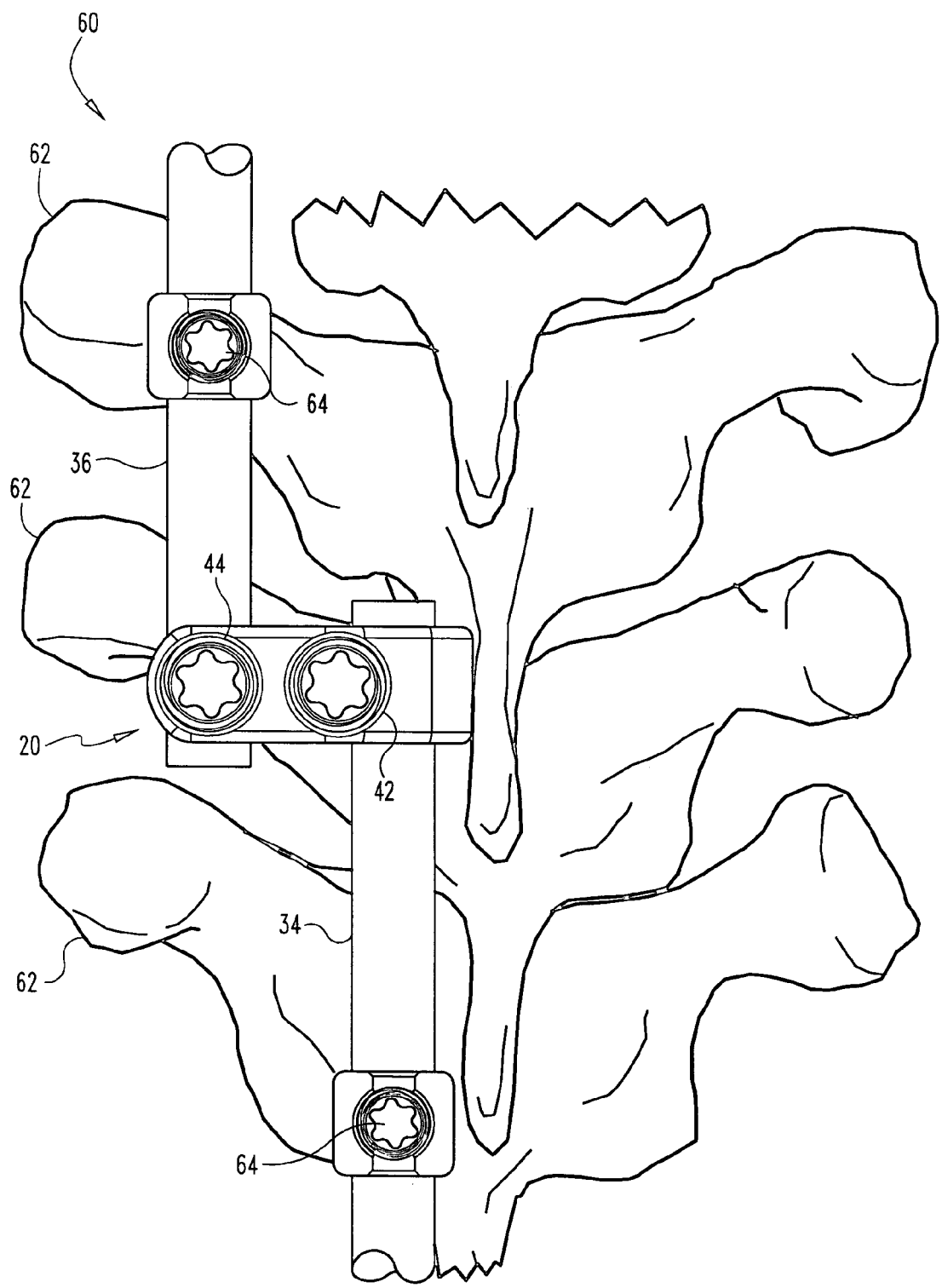
FIG. 5 is another perspective view of a connector assembly relative to vertebrae according to an embodiment of the present application.

FIG. 5 provides another perspective view of connector device 20 relative to vertebrae 62. In this embodiment, spinal rods 34 and 36 are positioned on the same side of the spinous processes of the vertebrae. In the previous illustration, spinal rods 34 and 36 are connected to at least one common vertebra. FIG. 5 illustrates a type of "vertical connection" where the principal or only point of connection between spinal rods 34 and 36 is connector device 20. The configuration of connector device 20 allows for a sturdy, stable "vertical connection" with both spinal rods on the same side of the spinal midline.

The use of connector device 20 will be described in certain embodiments as follows, with particular reference to a spinal orthopedic procedure. It will be appreciated that other uses of connector 20 in other surgical procedures could be made.

Once an appropriate access to a surgical site is obtained, connector 20 can be inserted to the surgical site, and may be placed in a desired position at or adjacent certain vertebra(e) 62. In certain embodiments, a surgical procedure may be needed to revise a prior surgery. In such cases, spinal rod 34 may be an existing spinal rod that was previously connected to vertebrae 62 via pedicle screws 64, and spinal rod 36 is to be introduced to the surgical site and connected to vertebrae 62. Connector device 20 may be loaded onto spinal rod 34 from a top direction, with rod 34 being positioned in channel 26 at a desired position along rod 34. Screw 42 is inserted into through-hole 38, so that threaded portion 43 engages with the threaded surface of through-hole 38. Screw 42 is advanced into through-hole 38 so as to bear against and push spinal rod 34 against inner contact surface 30. In the illustrated embodiment, bearing surface 46 of screw 42 contacts rod 34 to urge rod 34 against contact surface 30. Screw 42 is sufficiently tightened to engage and lock connector device 20 to spinal rod 34.

Rod 36 can be pre-loaded into or otherwise connected to connector device 20 before engagement of connector device 20 to spinal rod 34, or rod 36 can be loaded into or otherwise connected to connector device 20 after engagement of connector device 20 to spinal rod 34. Spinal rod 36 is loaded into connector device 20 by inserting an end of rod 36 through opening 28, and advancing rod 36 through opening 28 to a desired position. Screw 44 is inserted into and advanced through through-hole 40 so as to bear against and push spinal rod 36 against inner contact surface 32. Screw 44 is sufficiently tightened to engage connector device 20 to spinal rod 36. Screw 44 and second engagement portion 24 surround or encompass a segment of spinal rod 36. Final engagement is accomplished by tightening screws 42 and 44 against spinal rods 34 and 36, thereby locking the spinal rods laterally relative to each other. Spinal rod 36 can be connected to vertebrae 62 via pedicle screws 64. A vertebral fixation system involving connector device 20, spinal rods 34 and 36, and screws 42 and 44 is now in place, providing a rigid transverse connection between the adjacent spinal rods.

It will be appreciated that an existing rod (e.g. rod 34) can be received in opening 28 and a new rod (e.g. rod 36) can be received in channel 26. Thus, connector 20 can be maneuvered toward an end of rod 34 so that the particular end of rod 34 enters opening 28 and is adjacent contact surface 32 of connector 20. In the illustrated embodiment, connector 20 may not advance over pedicle screws 64, and thus connector 20 would be positioned between an end of rod 34 and the nearest pedicle screw 64 connecting rod 34 to a vertebra 62. Screw 44 can be threaded into connector 20 so as to loosely or tightly hold connector 20 to rod 34. If further adjustments of connector 20 with respect to rod 34 are expected or possible, then a loose holding of rod 34 can easily allow such adjustments, and tightening of screw 44 can occur after any final adjustments. Rod 36 can be placed in channel 26 either before or after connection of connector 20 to rod 34, and connector 20 (if loosely connected to rod 34) could be rotated or further maneuvered so that channel 26 is adjacent rod 36. Such rotation or maneuvering may be necessary if rod 34 has been fixed or otherwise connected to another implant or vertebra 62, and thus has less freedom of movement.

The above-described methods are useful both with the parallel dual-rod construct embodiment shown in FIG. 4, and with the approximately linear construct embodiment shown in FIG. 5. In the former, rods 34 and 36 are connected to one or more vertebrae 62 in common. In that situation, it may be difficult to insert a connector to provide lateral stabilization. Connector device 20, as noted above, provides for loading of one rod from a top direction, and for loading of the other through an opening in connector 20. Even if both rods 34 and 36 have already been placed, and are fixed to vertebrae 62, connector 20 can be used. For example, connector 20 may be maneuvered between rods 34 and 36 and the adjacent tissue so that connector 20 is positioned about rod 34, with rod 34 being positioned in channel 26, then connector 20 can be maneuvered so that an end of rod 36 enters opening 28. In that situation, connector 20 would be positioned about rod 36 at a position in between an end of rod 36 and the nearest pedicle screw 64 connecting rod 36 to a vertebra 62. With respect to the substantially linear construct embodiment of FIG. 5, connector 20 can essentially make one elongated member out of two. For example, in situations in which support or correction is needed along sections of the spine in which the size of the vertebrae change significantly, as between the cervical and thoracic vertebrae, a larger diameter rod can be connected to relatively lower vertebrae and a smaller diameter rod can be connected to relatively upper vertebrae Referring to FIG. 5, in that situation rod 34 may have a larger diameter than rod 36, and connector device 20 can connect different diameter rods into essentially one elongated member.

The parts of connector device 20 are composed of biocompatible materials that are also compatible with particular elongated members or other implants with which connector device 20 will be used. Thus, connector device 20 may be made of titanium, nickel, alloys of titanium and nickel, stainless steel, certain sturdy plastic materials, or other sturdy materials. The material(s) chosen for connector device 20 should be the same as those of the rods with which connector device 20 is used, or at least of a material that will not cause discomfort or an adverse reaction when used with the rods. It will be appreciated that materials other than those described above could also be used.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A connector apparatus for linking elongate members, comprising:
    a connector body having a top surface and a longitudinal axis, said body further having a C-shaped engagement portion contiguous with a closed engagement portion;
    wherein each of said engagement portions includes an opening configured to receive an elongate member, each of said openings defined by an inner contact surface configured to engage said corresponding elongate member, each of said engagement portions including a through-hole and a retaining member, and said opening corresponding to said C-shaped engagement portion includes an at least partially open bottom;
    wherein said through-holes extend through said top surface of said connector body and are aligned substantially perpendicular with said longitudinal axis of said connector body;
    wherein said through-hole and retaining member corresponding to said C-shaped engagement portion are offset from said corresponding elongate member when said elongate member is positioned in said corresponding opening;
    wherein said retaining members are operable to advance through said corresponding through-holes to contact said corresponding elongate members and urge said elongate members against said corresponding inner contact surfaces to engage said connector body to said elongate members with said elongate members comprising elongate spinal rods oriented substantially parallel with one another; and
    wherein said connector body includes an arcuate external surface extending from said top surface, curving around and laterally enclosing said opening corresponding to said C-shaped engagement portion, returning toward said closed engagement portion, and terminating in a bottom surface, said bottom surface positioned below said inner contact surface corresponding to said opening corresponding to said C-shaped engagement portion and extending across a portion of said opening corresponding to said C-shaped engagement portion.

2. The apparatus of claim 1, wherein said opening corresponding to said closed engagement portion is circular and said opening corresponding to said C-shaped engagement portion is a channel.

3. The apparatus of claim 1, wherein said closed engagement portion and said corresponding retaining member encompass a segment of said corresponding elongate member when said corresponding retaining member is advanced through said corresponding through-hole.

4. The apparatus of claim 1, wherein said through-holes are in communication with said corresponding openings.

5. The apparatus of claim 1, wherein said retaining member corresponding to said C-shaped engagement portion includes a curved bearing surface to fittingly contact said corresponding elongate member.

6. The apparatus of claim 1, wherein each of said retaining members is a screw.

7. The apparatus of claim 1, wherein said bottom surface extends substantially parallel to said top surface.

8. The apparatus of claim 1, wherein said closed engagement portion completely surrounds a segment of a corresponding one of said spinal rods positioned in said opening defined by said closed engagement portion.

9. A spinal fixation system, comprising:

first and second spinal rods;

a connector body to connect said spinal rods to each other, said body having a top surface and a first C-shaped engagement portion directly adjacent a second closed engagement portion, said first and second portions having corresponding first and second openings to receive said spinal rods, and wherein said opening corresponding to said closed engagement portion is circular and said opening corresponding to said C-shaped engagement portion is a bottom opening channel;

first and second screws to engage said connector body to said corresponding spinal rods;

wherein said engagement portions include corresponding first and second through-holes in communication with said corresponding openings and configured to receive said corresponding screws, said through-holes being aligned substantially at a right angle with said top surface of said connector body; and wherein said first screw is medially offset from said first spinal rod, said first screw being configured to advance through said first through-hole to engage said first spinal rod and urge said first spinal rod against a curved bearing surface defining said first opening, thereby engaging said connector body to said first spinal rod; and wherein said second screw is configured to advance through said second through-hole to engage said second spinal rod and urge said second spinal rod against a bearing surface defining said second opening, thereby engaging said connector body to said second spinal rod, with said first spinal rod oriented substantially parallel with said second spinal rod; and wherein said connector body includes an arcuate external surface curving around said channel and extending between said top surface and a linear bottom surface laterally offset from said first through-hole.

10. The system of claim 9, wherein each of said screws is a set screw.

11. The system of claim 9, wherein said first screw includes a curved bearing surface configured to contact said first spinal rod.

12. The system of claim 9, wherein each of said screws includes a recessed hexagonal top portion for receiving a screw insertion tool, said screws being configured to advance below said top surface of said connector body and rest within said through-holes.

13. The system of claim 9, wherein said through-holes extend through said top surface of said connector body to said corresponding openings.

14. The system of claim 9, wherein said linear bottom surface extends substantially parallel to said top surface.

15. The system of claim 9, wherein said second closed engagement portion completely surrounds a segment of said second spinal rod positioned in said second opening.

16. A method of linking spinal rods, comprising:

providing a connector apparatus having a top surface and a closed engagement portion adjacent a C-shaped engagement portion, said closed engagement portion having an opening defined by a first inner contact surface and said C-shaped engagement portion having a bottom opening channel defined by a second inner contact surface, each of said opening and said channel being configured to receive a spinal rod, each of said engagement portions including a through-hole substantially perpendicular with said top surface of said connector apparatus, each of said through-holes being configured to receive a screw to secure said apparatus to spinal rods, wherein said connector apparatus includes an arcuate external surface extending from said top surface, curving around and laterally enclosing said channel, returning toward said closed engagement portion, and terminating in a bottom surface, said bottom surface positioned below said second inner contact surface and extending across a portion of said channel;

inserting a first spinal rod in said opening in said closed engagement portion;

positioning said apparatus at a desired position proximal vertebrae and a second spinal rod;

maneuvering said apparatus so that said second spinal rod is received in said channel;

engaging said connector apparatus to said first and second spinal rods with said first spinal rod oriented substantially parallel with said second spinal rod; and connecting said first spinal rod to vertebrae.

17. The method of claim 16, comprising providing a first screw and a second screw, wherein said connector body includes a first through-hole in communication with said opening and a second through-hole in communication with said channel, wherein said engaging comprises advancing said first screw through said first through-hole and advancing said second screw through said second through-hole.

18. The method of claim 17, wherein said second through-hole and said second screw are offset from said second spinal rod when said second spinal rod is positioned in said channel.

19. The method of claim 18, comprising said second screw urging said second spinal rod against said second inner contact surface to engage said connector apparatus to said second spinal rod.

20. The method of claim 16, wherein said bottom surface extends substantially parallel to said top surface.

21. The method of claim 16, wherein said closed engagement portion completely surrounds a segment of said first spinal rod positioned in said first opening.

* * * * *